US012109320B2

(12) United States Patent
Abbaszadegan et al.

(10) Patent No.: US 12,109,320 B2
(45) Date of Patent: Oct. 8, 2024

(54) PATHOGEN-INACTIVATING FACIAL MASK

(71) Applicants: Morteza Abbaszadegan, Chandler, AZ (US); Absar Alum, Mesa, AZ (US)

(72) Inventors: Morteza Abbaszadegan, Chandler, AZ (US); Absar Alum, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 629 days.

(21) Appl. No.: 17/320,983

(22) Filed: May 14, 2021

(65) Prior Publication Data

US 2021/0353790 A1    Nov. 18, 2021

Related U.S. Application Data

(60) Provisional application No. 63/025,695, filed on May 15, 2020.

(51) Int. Cl.
| | |
|---|---|
| *A62B 18/02* | (2006.01) |
| *A61L 2/04* | (2006.01) |
| *A62B 7/10* | (2006.01) |
| *A62B 9/00* | (2006.01) |
| *A62B 18/08* | (2006.01) |
| *A62B 23/02* | (2006.01) |
| *A62B 23/06* | (2006.01) |
| *H05B 1/02* | (2006.01) |

(Continued)

(52) U.S. Cl.
CPC ........................... *A61L 2/04* (2013.01); *A62B 7/10* (2013.01); *A62B 9/003* (2013.01); *A62B 18/025* (2013.01); *A62B 18/08* (2013.01); *A62B 23/025* (2013.01); *A62B 23/06* (2013.01); *H05B 1/025* (2013.01); *H05B 3/18* (2013.01); *H05B 3/34* (2013.01); *A61L 2202/14* (2013.01); *A62B 18/084* (2013.01); *H05B 2203/02* (2013.01)

(58) Field of Classification Search
CPC ... A62B 18/084; A62B 18/025; A62B 23/025; A62B 7/10; A62B 9/003; A62B 18/08; A62B 23/06; A62B 23/02; A41D 13/1161; A41D 13/1192; A41D 13/11; A41D 13/00; A41D 13/1107; A41D 13/1138; A41D 13/1146; A41D 13/1176; H05B 3/18; H05B 1/025; H05B 3/34; H05B 2203/02; C03C 13/04; A61L 2/04; A61L 2202/14; A61L 9/18
See application file for complete search history.

(56) References Cited

U.S. PATENT DOCUMENTS

| | | | |
|---|---|---|---|
| 4,671,268 A | 6/1987 | Hunt | |
| 4,793,343 A * | 12/1988 | Cummins, Jr. | ........ A62B 18/08 219/501 |
| 5,165,395 A | 11/1992 | Ricci | |

(Continued)

FOREIGN PATENT DOCUMENTS

| | | | | |
|---|---|---|---|---|
| CN | 212139424 | * | 2/2020 | ............. A41D 13/11 |
| JP | 2021168769 A | * | 4/2020 | ............. A41D 13/11 |

(Continued)

*Primary Examiner* — Ophelia A Hawthorne
(74) *Attorney, Agent, or Firm* — Snell & Wilmer L.L.P.

(57) ABSTRACT

A facial mask having pathogen inactivation capabilities is disclosed. One embodiment comprises a mask and a pathogen inactivation system coupled to the mask. The pathogen inactivation system is configured to heat and inactivate bacteria and viruses.

16 Claims, 7 Drawing Sheets

(51) Int. Cl.
*H05B 3/18* (2006.01)
*H05B 3/34* (2006.01)

(56) References Cited

U.S. PATENT DOCUMENTS

2010/0175694 A1   7/2010  James et al.
2011/0297152 A1  12/2011  Duveen et al.
2017/0119991 A1   5/2017  Duveen et al.

FOREIGN PATENT DOCUMENTS

KR    20110045783 A  * 10/2009  ............. A62B 18/02
KR    20190067802 A  *  9/2017  ............. A62B 18/02

* cited by examiner

PATHOGEN-INACTIVATING FACIAL MASK

CROSS-REFERENCE TO RELATED APPLICATIONS

This application is a non-provisional of, and claims priority to, and the benefit of U.S. Provisional Application No. 63/025,695 entitled "Pathogen-Inactivating Facial Mask" filed on May 15, 2020. The disclosure of the foregoing application is incorporated herein by reference in its entirety, including but not limited to those portions that specifically appear hereinafter, but except for any subject matter disclaimers or disavowals, and except to the extent that the incorporated material is inconsistent with the express disclosure herein, in which case the language in this disclosure shall control.

TECHNICAL FIELD

The present disclosure relates to facial masks, and in particular to facial masks comprising a pathogen inactivation system.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, pathogens may be projected from one individual towards another individual, via a sneeze, a cough, or the like. Thus, improved sanitization products may be desirable.

SUMMARY

A facial mask is disclosed herein. The facial mask may comprise: a mask; and a pathogen inactivation system coupled to the mask, the pathogen inactivation system configured to heat and inactivate bacteria and viruses.

In various embodiments, the pathogen inactivation system comprises a heating element. The mask may comprise an inner layer and an outer layer; and the heating element may be disposed between the inner layer and the outer layer. The facial mask may further comprise a filter layer. The filter layer may be disposed between the outer layer and the inner layer. The pathogen inactivation system may further comprise a heating element embedded within the mask. The heating element may be at least one of a nichrome wire and a positive temperature coefficient (PTC) resistor. The pathogen inactivation system may further comprise an input source; and the input source may electrically couple a power supply to the heating element. The heating element may be activated in response to the power supply being electrically coupled to the input source. The pathogen inactivation system may further comprise a power source; and the power source may be configured to be charged in response to the power supply being coupled to the input source. The power source may be configured to power the heating element while the facial mask is worn by a user.

A pathogen inactivation system is disclosed herein. The pathogen inactivation system may comprise: a heating element configured to be disposed in a facial mask; and a controller in electrical communication with the heating element, the controller configured to activate the heating element and inactivate pathogens that are proximate the heating element.

In various embodiments, the pathogen inactivation system may further comprise a sensor in electrical communication with the controller, the sensor configured to provide at least one of bacterial and viral data to the controller. The controller may be configured to determine a pathogen amount exceeds a pre-determined pathogen threshold, and the controller is configured to activate the heating element in response to the determining the pathogen amount exceeds the pre-determined pathogen threshold. The pathogen inactivation system may further comprise an input source, wherein the input source is configured to couple to a power supply and activate the heating element to clean the facial mask. The pathogen inactivation system may further comprise a power source in electrical communication with the controller, wherein the power source is rechargeable. The power source may be portable.

A nose plug apparatus is disclosed herein. The nose plug apparatus may comprise: a first plug; and a pathogen inactivation system including a first heating element coupled to the first plug, the first heating element configured to receive an electrical current to heat the first plug and inactivate pathogens proximate the first plug.

In various embodiments, the nose plug apparatus may further comprise a second plug, wherein the pathogen inactivation system further comprises a second heating element coupled to the second plug. The first heating element may be embedded within the first plug and the second heating element is embedded within the second plug.

The contents of this section are intended as a simplified introduction to the disclosure, and are not intended to limit the scope of any claim.

BRIEF DESCRIPTION OF THE DRAWINGS

With reference to the following description and accompanying drawings.

DETAILED DESCRIPTION

The following description is of various exemplary embodiments only, and is not intended to limit the scope, applicability, or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, the connecting lines shown in various figures contained herein are intended to represent exemplary functional relationships and/or physical couplings between various elements. It should be noted that many alternative or additional functional relationships or physical connections may be present in inflatable actuators, soft robotic systems, and/or the like.

Disclosed herein is a pathogen inactivation system. In various embodiments, the pathogen inactivation system is for use in a facial mask and configured to inactivate pathogens disposed proximate to, or projected towards, the facial mask. In various embodiments, the pathogen inactivation system may comprise one or more of a voltage converter, a charging module, a power source, an electronics module, and/or a heating element.

In various embodiments, the facial mask is configured to continuously inactivate viruses and bacteria to minimize exposure to these airborne pathogens. The disclosed facial mask may provide the population with protection and/or decreased exposure to respiratory viruses, such as coronavirus, and/or bacteria, such as Legionella bacteria. In various embodiments, the disclosed facial mask is configured for continuous inactivation of viruses and/or bacteria by communicating air through one or more heating elements embedded in the facial mask.

Figure 1:
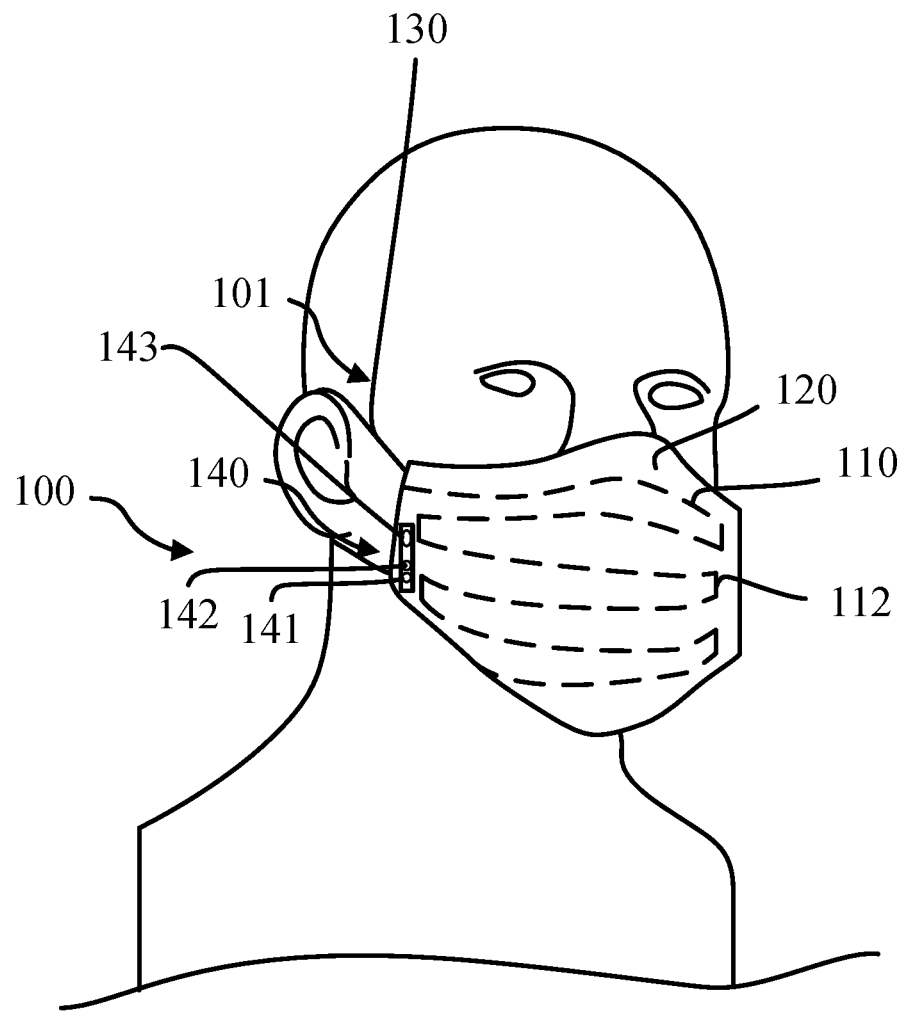
FIG. 1 illustrates a perspective view of an exemplary facial mask having a pathogen inactivation system, in accordance with an exemplary embodiment.

Referring now to FIG. 1, a facial mask 100 comprising a pathogen inactivation system 101 is illustrated, in accordance with various embodiments. In various embodiments, the pathogen inactivation system 101 comprises a heating element 110. In various embodiments, the heating element 110 is disposed within the facial mask 100 (i.e., embedded in the facial mask 100). The heating element 110 may be configured to provide continuous heat to ambient air passing near, in, and/or through the facial mask 100. In various embodiments, the heating element 110 is capable of heating ambient air and/or the surface of the facial mask to a temperature capable of inactivating airborne viruses and/or bacteria. In various embodiments, the pathogen inactivation system 101 of the facial mask 100 is configured for synchronized filtration and heating of ambient air to simultaneously capture and inactivate pathogens, such as viruses and/or bacteria.

In various embodiments, the facial mask 100 comprises a mask 120, a first strap 130 and a second strap. The mask 120 is configured to cover a nose and a mouth of a user 10, in accordance with various embodiments. The first strap 130 is configured to secure the facial mask to a first ear of the user 10. The second strap is in accordance with the first strap 130 and is configured to secure the facial mask 100 to a second ear of the user 10. The type of mask 120 is not limited by this disclosure. For example, various masks, such as an N95 mask, a surgical mask, a paper mask, or a cloth mask are within the scope of this disclosure.

In various embodiments, the heating element 110 can be integrated into the fabric of the facial mask 100. In various embodiments, the heating element 110 can be integrated into a device insertable into nasal cavities as described further herein. In various embodiments, the heating element 110 can be retrofit to existing masks. In various embodiments, the heating element 110 can be inserted in facial masks configured to receive an insertable filter. Both insertable and non-insertable embodiments of the present disclosure may be configured to continuously inactivate viruses and/or bacteria. In various embodiments, the heating element 110 comprises one or more active and/or passive components such as nichrome, conductive paste, heating polymers, and/or any other suitable heating element. In various embodiments, the heating element 110 comprises a wire 112 embedded within the mask 120. In various embodiments, the wire 112 may comprise a nichrome wire, a positive temperature coefficient (PTC) resistor, or any other suitable wire configured to generate heat in response to an electrical current.

In various embodiments, the wire 112 may be routed in various shapes or configurations within the mask 120. For example, the wire 112 may be routed in a horizontal serpentine type pattern (i.e., proximate one ear of the user 10 towards the other ear of a user 10 and back as in FIG. 1), in a vertical serpentine type pattern (i.e., proximate a top portion of mask 120 towards a bottom portion of mask 120 and back as in facial mask 200 in FIG. 2), or in a mesh type pattern as illustrated in facial mask 300 in FIG. 3. Although illustrated in various routings/configurations the present disclosure is not limited in this regard. A routing of wire 112 may be a design choice and varied based on a desired amount of pathogen inactivation, in accordance with various embodiments.

In various embodiments, the mask 120 is configured to house, or contain, electrical components for the pathogen inactivation system 101. For example, the mask 120 may house a battery, a microcontroller, the heating element 110, various circuitry, etc., in accordance with various embodiments. Although illustrated as housing the electrical components in the mask 120, the present disclosure is not limited in this regard. For example, a portion of the electrical components may be stored in first strap 130, the second strap, or any other component of the facial mask 100, in accordance with various embodiments.

In various embodiments, the heating element 110 uses either a continuous portable power supply, a plug-in based format, or a combination of the two as described further herein. The continuous portable power supply may be configured for a facial mask 100 that provides continuous pathogen inactivation during use. For example, the pathogen inactivation system 101 may include a heating module 140 that is coupled to a portable power supply, such as a battery as described further herein. The heating module 140 may comprise an input source 143. In various embodiments, the input source 143 may be in electrical communication with a controller. The controller is in electrical communication with, and configured to operate, the heating element 110. In various embodiments, a battery may be removable from the facial mask 100 and chargeable separate from the facial mask 100 via the input source 143. In various embodiments, the heating module 140 may be fixedly coupled to the facial mask 100.

In various embodiments, a plug-in power supply may be configured for a reusable facial mask, such that the facial mask could be plugged in and cleaned after use. For example, the input source 143 may be electrically coupled to a controller and configured to receive an input source, such as an alternating current (A/C) or a direct current (D/C) input source when the facial mask 100 is not in use. In various embodiments, in response to receiving a current through the input source 143, the heating module 140 may be configured to activate the heating element 110. In various embodiments, in a combined configuration, the heating module 140 may be configured to activate the heating element 110 and charge a portable power supply as described further herein. In this regard, the facial mask 100 be activated when not in use by the input source and clean the respective facial mask 100, while simultaneously charging the portable power supply to provide power to the heating element while the facial mask is in use, in accordance with various embodiments.

The heating module 140 may be configured to display various lights when the pathogen inactivation system 101 is in use. For example, a first light 141 may be display in a red color when the pathogen inactivation system 101 is not in use, a second light 142 may be configured to display a green color when the pathogen inactivation system 101 is activated, or the like. Any number of color combinations or light combinations/display is within the scope of this disclosure.

Figure 2:
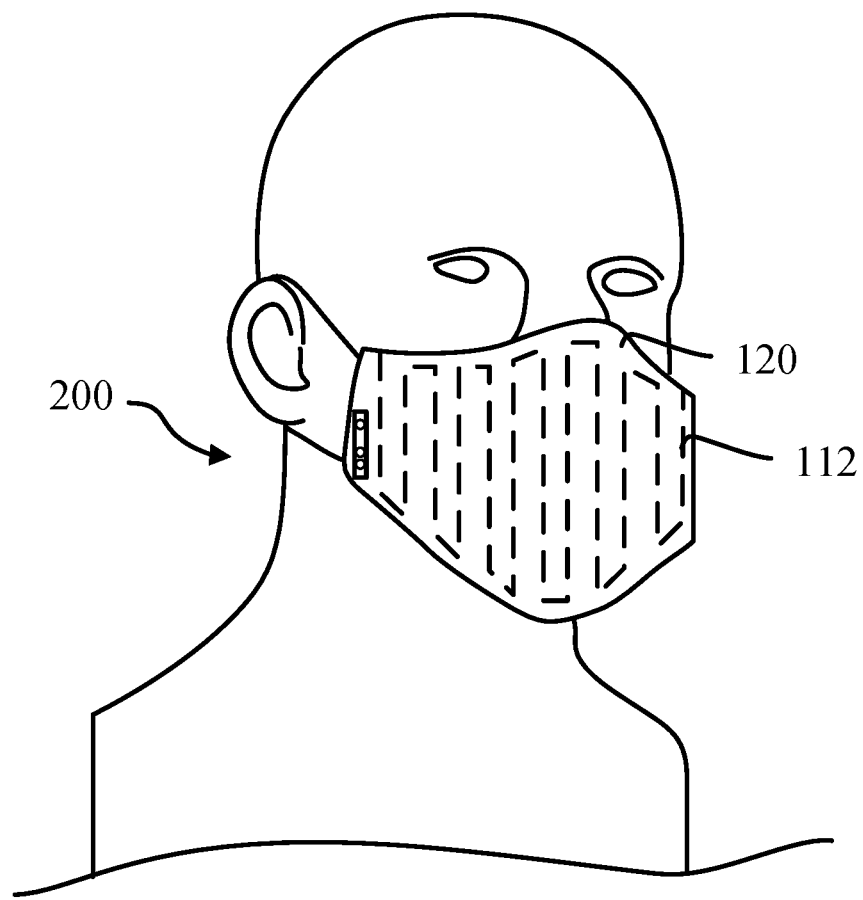
FIG. 2 illustrates a perspective view of an exemplary facial mask having a pathogen inactivation system, in accordance with an exemplary embodiment.
Figure 3:
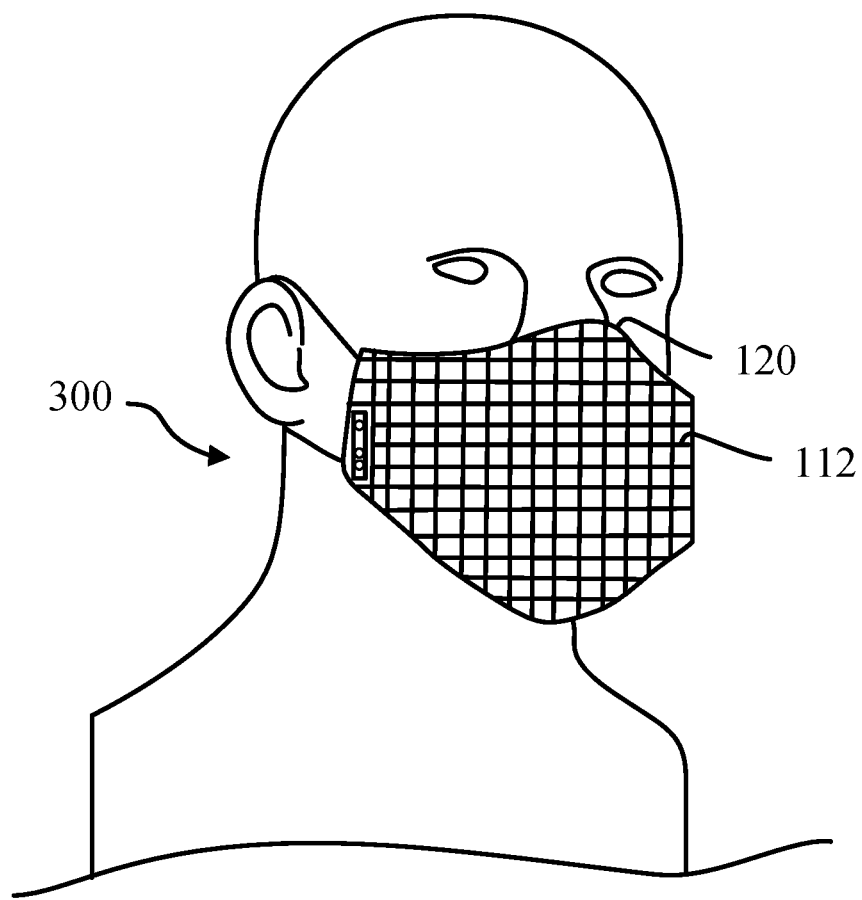
FIG. 3 illustrates a perspective view of an exemplary facial mask having a pathogen inactivation system, in accordance with an exemplary embodiment.
Figure 4:
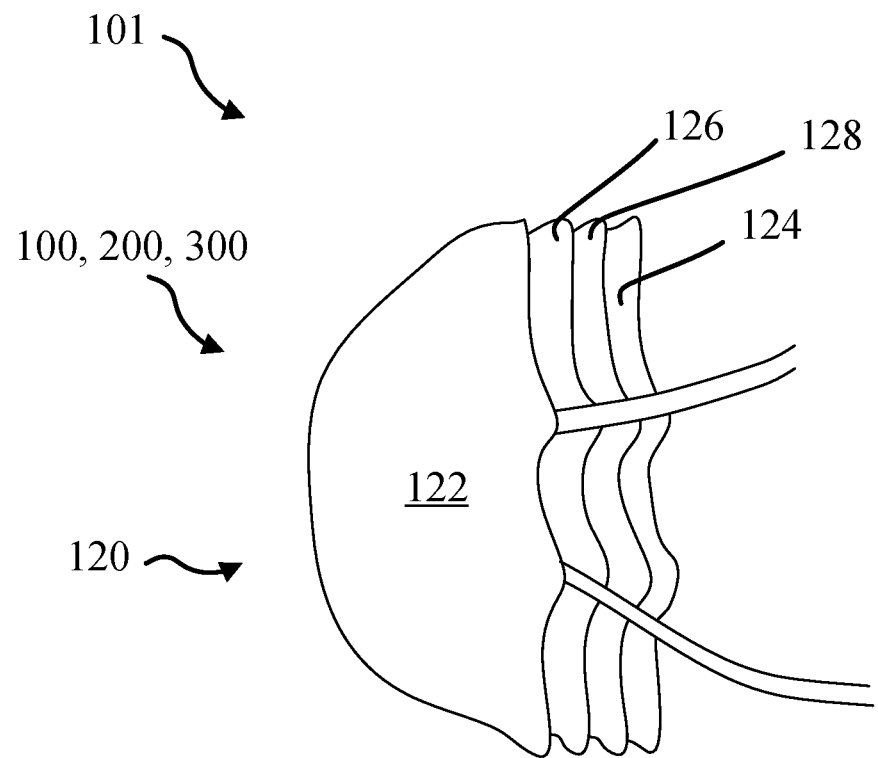
FIG. 4 illustrates a partially exploded view of an exemplary facial mask having a pathogen inactivation system, in accordance with an exemplary embodiment.

Referring now to FIG. 4, a side partially exploded view of a facial mask 100, 200, 300 with a pathogen inactivation system 101 is illustrated, in accordance with various embodiments. The mask 120 of the facial mask 100, 200, 300 may be composed of various layers. For example, the mask 120 may comprise an outer layer 122 and an inner layer 124. The outer layer 122 and inner layer 124 may each comprise a non-woven polypropylene material, in accordance with various embodiments. Although described herein as comprising a polypropylene material, the outer layer 122 and inner layer 124 are not limited in this regard and may comprise various materials as one skilled in the art will recognize. In various embodiments, the inner layer 124 and outer layer 122 may comprise different materials. In various embodiments, the heating element 110 from FIGS. 1-3 is disposed between the outer layer 122 and the inner layer 124. In this regards, the heating element 110 may be embedded within the mask 120, in accordance with various embodiments.

In various embodiments, the mask 120 may comprise additional layers. Although illustrated as including four layers, the mask 120 is not limited in this regard. For example, the mask 120 may comprise at least two layers (i.e., outer layer 122 and inner layer 124) and any number of additional layers as desired. In various embodiments, the mask 120 comprises a filter layer 126. The filter layer 126 may be disposed between the outer layer 122 and the inner layer 124 in accordance with various embodiments. In various embodiments, a non-woven polypropylene melt blown layer. In various embodiments, the heating element 110 may be embedded within the filter layer 126. In this regard, the filter layer 126 may be an independent component of facial mask 100, 200, 300 and be insertable within the facial mask 100, 200, 300, in accordance with various embodiments.

In various embodiments, any additional mask features, such as a reusable respirator, a gas and vapor cartridge, a respirator filter, a respirator pre-filter, or the like may be a layer for the mask 120 and be within the scope of this disclosure. In various embodiments, the mask 120 may comprise a support layer 128. The support layer 128 may be disposed between the filter layer 126 and the inner layer 124. However, the support layer 128 is not limited in this regard and may be disposed between the filter layer 126 and the outer layer 122, in accordance with various embodiments.

In various embodiments, the heating element 110 may be disposed between any two layers (i.e., between the outer layer 122 and the filter layer 126, between the filter layer 126 and the support layer 128, between the support layer 128 and the inner layer 124, etc.).

Figure 5:
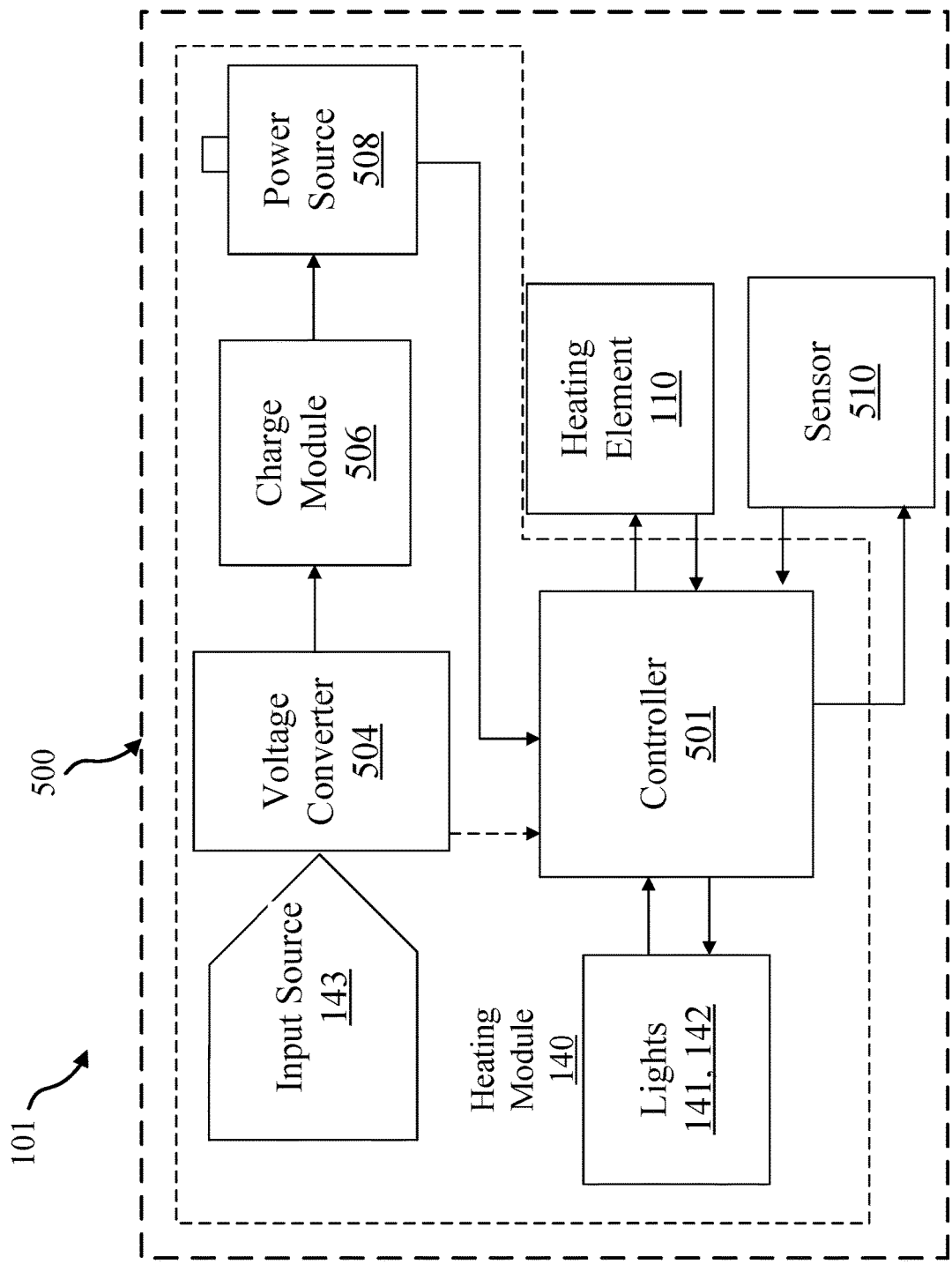
FIG. 5 illustrates a control module for an exemplary pathogen inactivation system, in accordance with various embodiments.

Referring now to FIG. 5, a control system 500 for pathogen inactivation system 101 is illustrated, in accordance with various embodiments. In various embodiments, the control system 500 includes the heating module 140 from FIG. 1. In various embodiments, the heating module 140 comprises a controller 501.

In various embodiments, controller 501 may be configured as a central network element or hub to access various systems and components of pathogen inactivation system 101. Controller 501 may comprise a network, computer-based system, and/or software components configured to provide an access point to various systems and components of pathogen inactivation system 101. In various embodiments, controller 501 may comprise a processor. In various embodiments, controller 501 may be implemented in a single processor. In various embodiments, controller 501 may be implemented as and may include one or more processors and/or one or more tangible, non-transitory memories and be capable of implementing logic. Each processor can be a general purpose processor, a digital signal processor (DSP), an application specific integrated circuit (ASIC), a field programmable gate array (FPGA) or other programmable logic device, discrete gate or transistor logic, discrete hardware components, or any combination thereof. Controller 501 may comprise a processor configured to implement various logical operations in response to execution of instructions, for example, instructions stored on a non-transitory, tangible, computer-readable medium configured to communicate with controller 501. In various embodiments, the controller 501 comprises electronics such as a microprocessor, an integrated circuit, and/or passive and active components. In various embodiments, the electronics are used to select optimal operational parameters, for example, temperature or duration of heating.

System program instructions and/or controller instructions may be loaded onto a non-transitory, tangible computer-readable medium having instructions stored thereon that, in response to execution by a controller, cause the controller to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

In various embodiments, the heating module 140 comprises the input source 143, a voltage converter 504, and the controller 501. In various embodiments, the heating module 140 further comprises a charge module 506 and a power source 508 (i.e., a portable power supply, such as a battery or the like). In various embodiments, the charge module 506 is configured to control a charge rate for the power source 508. In this regard, the charge module 506 may ensure the power source 508 is properly charged. In various embodiments, a plug-in only configuration for the heating module 140 may include the input source 143, the voltage converter 504, and the controller 501. In this regard, in a plug-in only configuration, the charge module 506 and the power source 508 may be eliminated. In various embodiments, the voltage converter 504 is configured to charge and/or store energy for supplying to the controller 501 of heating module 140. The heating module 140 may be configured to receive AC input of between about 100V to about 240V via the input source 143. The heating module may be configured to receive DC input of between about 1V to about 48V via the input source 143. In various embodiments, the DC input may be provided by a USB charging port, a car battery, or any other suitable DC power supply. In various embodiments, the power source is provided directly from the input source.

In various embodiments, the control system 500 further comprises a sensor 510. In various embodiments, the sensor 510 is a component of the heating module 140. In various embodiments, the sensor 510 is embedded in the mask 120 from FIGS. 1-3. In various embodiments, the sensor 510 comprises a biosensor (i.e., a sensor configured to provide bacterial and/or viral data to the controller). In various embodiments, the sensor 510 is in electrical, and operable, communication with the controller 501. In various embodiments, the controller 501 is configured to determine, based on the bacterial and/or viral data, whether a pre-determined threshold of pathogens is proximate the mask 120 from FIGS. 1-3. In this regard, in response to controller 501 determining the pre-determined threshold of pathogens is exceeded, the controller 501 may command heating element 110 to operate for a pre-determined period of time. In various embodiments, the controller 501 may be configured to determine an amount of time based on a number of pathogens determined by sensor 510.

In various embodiments, the control system further comprises the lights 141, 142 from FIG. 1. The lights 141, 142 may be in electrical communication with controller 501. In various embodiments, the controller may activate one of lights 141, 142, in response to activating the heating element 110. In this regard, a user may see a visual indication that the facial mask 100, 200, 300 from FIGS. 1-3 is being cleaned, or a person proximate the user may see a visual indication indicating the facial mask 100, 200, 300 from FIGS. 1-3 is being cleaned.

Figure 6:
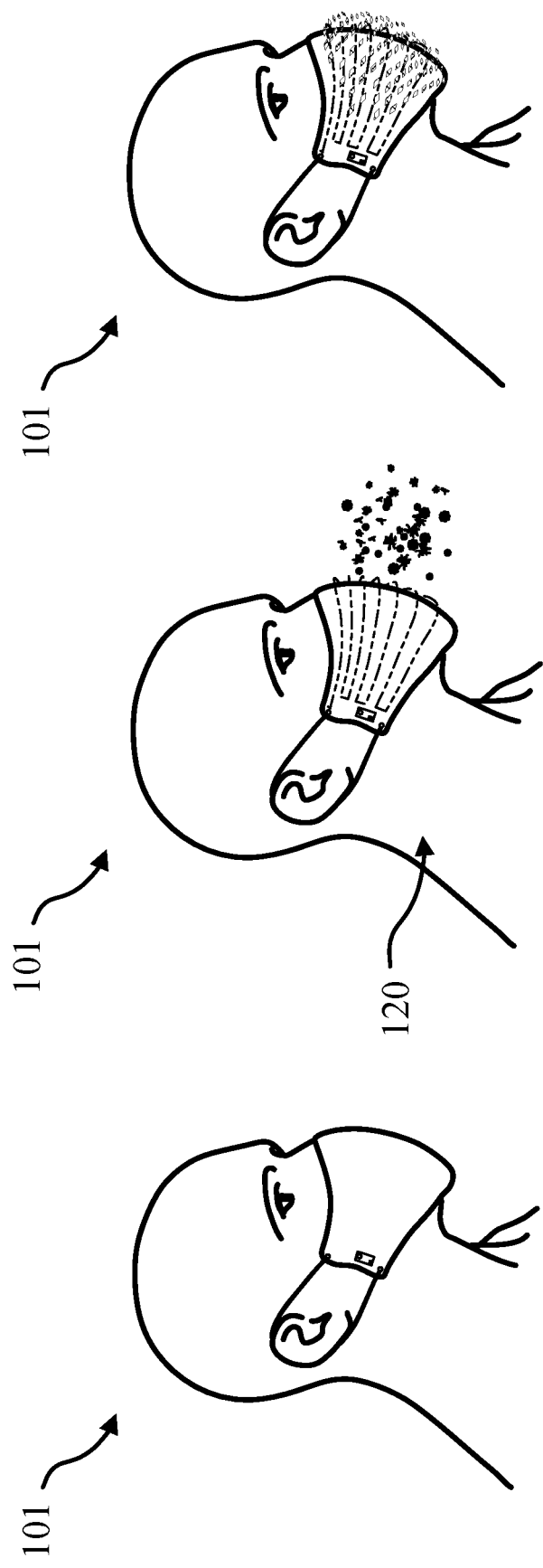
FIG. 6A illustrates a perspective view of an exemplary pathogen inactivation system during use, in accordance with an exemplary embodiment.
FIG. 6B illustrates a perspective view of an exemplary pathogen inactivation system during use, in accordance with an exemplary embodiment.
FIG. 6C illustrates a perspective view of an exemplary pathogen inactivation system during use, in accordance with an exemplary embodiment.

Referring now to FIGS. 6A-6C, a pathogen inactivation system 101 is illustrated in active use, in accordance with various embodiments. In various embodiments, the pathogen inactivation system 101 may be in a deactivated state initially (i.e., passive, powered down, non-activated, and/or otherwise not actively killing pathogens), as illustrated in FIG. 6A. As pathogens approach an outer surface of the mask 120, a sensor (e.g., sensor 510 from FIG. 5) may send bacterial and/or viral data to a controller (e.g., controller 501 from FIG. 5). In response to the controller (e.g., controller 501 from FIG. 5) determining the pathogens exceed a pre-determined threshold of pathogens, the controller may activate the pathogen inactivation system 101 (i.e., controller 501 may send an electrical current through heating element 110 resulting in the pathogens being heated) as illustrated in FIG. 6B. In various embodiments, the heating element 110 may be heated for a time based on the bacterial and/or viral data or based on a pre-determined time. In various embodiments, in response to the heating element 110 increasing a temperature of the pathogens from FIG. 6B, the heating element 110 may inactivate the pathogens.

For example, preliminary testing has shown that the disclosed pathogen inactivation system 101 causes rapid inactivation of viruses and bacteria. Air comprising a concentration of microorganisms higher than is normally present in ambient air were exposed to the heating element and were inactivated. The preliminary performance evaluation testing resulted in a rapid inactivation of viral materials and bacterial cells as they came in contact with the face mask embedded with a heating element 110. The test microorganisms included viral surrogate and both gram-positive and gram-negative bacterial species (Table 1).

TABLE 1

Viral and bacterial inactivation on a face mask embedded with heating elements

| Microorganism | Name | Type | $Log_{10}$ Reduction |
|---|---|---|---|
| Virus | Bacteriophage P22 | DNA Virus | >2.00 $Log_{10}$ |
| Bacteria | *Escherichia coli* | Gram-negative | >2.00 $Log_{10}$ |
|  | *Pseudomonas aeruginosa* | Gram-negative | >2.00 $Log_{10}$ |
|  | *Staphylococcus aureus* | Gram-positive | >2.00 $Log_{10}$ |

The pathogen inactivation system 101 was found to be equally effective against viruses and both Gram-negative and Gram-positive bacteria. Because the antimicrobial capability of the technology is not dependent on a chemical agent, the inactivation mechanism does not contribute to the development of antimicrobial resistance. Rather, exemplary embodiments utilize physical disruption of viral particles and bacterial cells. The antimicrobial efficacy does not dissipate over time and continues to act at a consistent level during use.

Figure 7:
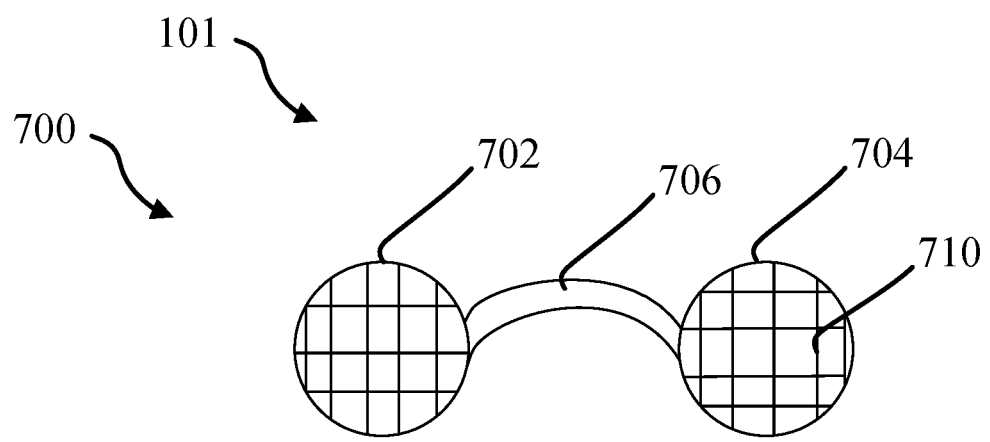
FIG. 7 illustrates a bottom up view of an exemplary nose plug having a pathogen inactivation system, in accordance with an exemplary embodiment.

Referring now to FIG. 7, a bottom up view of a nose plug 700 having the pathogen inactivation system 101 from FIGS. 1-6C is illustrated in accordance with various embodiments. Although illustrated as including a heating element 710 having a mesh in accordance with facial mask 300 from FIG. 3, the nose plug 700 is not limited in this regard. The heating element 710 may be oriented in various shapes and sizes. Although illustrated as having a first plug 702 and a second plug 704 coupled together by a bridge 706, the nose plug 700 is not limited in this regard. For example, nose plug 700 may comprise independent and distinct plugs 702, 704 without the bridge 706, in accordance with various embodiments. In various embodiments, the nose plug 700 includes the control system 500 from FIG. 5 for the pathogen inactivation system.

In various embodiments, the heating element 710 is embedded within the plugs 702, 704. In various embodiments, the plugs 702, 704 may include a cavity, or recess disposed therein and configured to receive the heating element 710.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A facial mask comprising:
   a mask further comprising:
      a non-woven polypropylene outer layer;
      a non-woven polypropylene inner layer; and
      a heating element disposed between the non-woven polypropylene outer layer and the non-woven polypropylene inner layer, the heating element having a nichrome wire; and
   a pathogen inactivation system coupled to the mask, the pathogen inactivation system configured to heat and inactivate at least one of bacteria or viruses.

2. The facial mask of claim 1, wherein:
   the pathogen inactivation system further comprises an input source; and
   the input source electrically couples a power supply to the heating element.

3. The facial mask of claim 2, wherein the heating element is activated in response to the power supply being electrically coupled to the input source.

4. The facial mask of claim 2, wherein:
   the pathogen inactivation system further comprises a power source; and
   the power source is configured to be charged in response to the power supply being coupled to the input source.

5. The facial mask of claim 4, wherein the power source is configured to power the heating element while the facial mask is worn by a user.

6. The facial mask of claim 1, wherein the pathogen inactivation system is configured to activate the heating element.

7. The facial mask of claim 6, wherein the mask further comprises a non-woven polypropylene melt blown filter layer.

8. The facial mask of claim 7, wherein the non-woven polypropylene melt blown filter layer is disposed between the non-woven polypropylene outer layer and the non-woven polypropylene inner layer and comprises the heating element.

9. The facial mask of claim 1, wherein the pathogen inactivation system further comprises:
   a first light configured to display a red color in response to the pathogen inactivation system being in a de-activated state; and
   a second light configured to display a green color in response to the pathogen inactivation system being in an activated state.

10. A pathogen inactivation system, comprising:
    a facial mask further comprising:
       a non-woven polypropylene outer layer;
       a non-woven polypropylene inner layer; and
       a heating element disposed between the non-woven polypropylene outer layer and the non-woven polypropylene inner layer, the heating element having a nichrome wire; and
    a controller in electrical communication with the heating element, the controller configured to activate the heating element and inactivate pathogens that are proximate the heating element.

11. The pathogen inactivation system of claim 10, further comprising a sensor in electrical communication with the controller, the sensor configured to provide at least one of bacterial and viral data to the controller.

12. The pathogen inactivation system of claim 11, wherein the controller is configured to determine a pathogen amount exceeds a pre-determined pathogen threshold, and the controller is configured to activate the heating element in response to the determining the pathogen amount exceeds the pre-determined pathogen threshold.

13. The pathogen inactivation system of claim 10, further comprising a power source in electrical communication with the controller, wherein the power source is rechargeable.

14. The pathogen inactivation system of claim 13, wherein the power source is portable.

15. The pathogen inactivation system of claim 10, wherein the heating element is configured to electrically couple to a power supply and activate to clean the facial mask.

16. The pathogen inactivation system of claim 10, further comprising:
    a first light configured to display a red color in response to the pathogen inactivation system being in a de-activated state; and
    a second light configured to display a green color in response to the pathogen inactivation system being in an activated state.

* * * * *